United States Patent
Wendland et al.

(10) Patent No.: US 9,772,321 B2
(45) Date of Patent: Sep. 26, 2017

(54) BENZOTHIAZOL-2-YLAZO-PHENYL COMPOUND AS DYE, COMPOSITIONS INCLUDING THE DYE, AND METHOD OF DETERMINING DEGREE OF CURE OF SUCH COMPOSITIONS

(71) Applicant: 3M INNOVATIVE PROPERTIES COMPANY, St. Paul, MN (US)

(72) Inventors: Michael S. Wendland, North St. Paul, MN (US); Mark F. Schulz, Lake Elmo, MN (US); Kathleen S. Shafer, Woodbury, MN (US); George W. Griesgraber, Eagan, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 69 days.

(21) Appl. No.: 14/777,033

(22) PCT Filed: Mar. 13, 2014

(86) PCT No.: PCT/US2014/026289
§ 371 (c)(1),
(2) Date: Sep. 15, 2015

(87) PCT Pub. No.: WO2014/151708
PCT Pub. Date: Sep. 25, 2014

(65) Prior Publication Data
US 2016/0041143 A1    Feb. 11, 2016

Related U.S. Application Data

(60) Provisional application No. 61/793,001, filed on Mar. 15, 2013.

(51) Int. Cl.
*G01N 33/44* (2006.01)
*C07D 277/82* (2006.01)
*C08K 3/22* (2006.01)
*C08K 3/26* (2006.01)
*C08K 3/34* (2006.01)
(Continued)

(52) U.S. Cl.
CPC ......... *G01N 33/442* (2013.01); *C07D 277/82* (2013.01); *C08K 3/22* (2013.01); *C08K 3/26* (2013.01); *C08K 3/34* (2013.01); *C08K 3/346* (2013.01); *C08K 3/38* (2013.01); *C08L 33/04* (2013.01); *C08L 41/00* (2013.01); *C09B 29/00* (2013.01); *C09B 43/263* (2013.01); *C09B 43/28* (2013.01); *C09B 69/106* (2013.01); *C08K 2003/2227* (2013.01); *C08K 2003/2244* (2013.01); *C08K 2003/265* (2013.01); *C08K 2003/267* (2013.01); *C08K 2003/387* (2013.01); *C09B 29/0088* (2013.01)

(58) Field of Classification Search
CPC .......... C07D 277/82; C08K 2003/2227; C08K 2003/2244; C08K 2003/265; C08K 2003/267; C08K 2003/387; C08K 3/22; C08K 3/26; C08K 3/34; C08K 3/346; C08K 3/38; C08L 33/04; C08L 41/00; C09B 29/00; C09B 43/263; C09B 43/28; C09B 69/106; C09B 29/0088; G01N 33/442
USPC ... 436/92, 96, 106, 108, 109, 111, 117, 119, 436/135, 164, 166; 252/408.1; 522/168; 524/405, 413, 425, 430, 445, 449, 451, 524/456, 726; 525/279; 534/778
See application file for complete search history.

(56) References Cited

U.S. PATENT DOCUMENTS 2,891,942 A    6/1959    Merian
3,207,614 A    9/1965    Canevari
(Continued)

FOREIGN PATENT DOCUMENTS

CN    101328320    12/2008
CN    103113759    5/2013
(Continued)

OTHER PUBLICATIONS

Cojocariu et al. Journal of Materials Chemistry, vol. 14, 2004, pp. 2909-2916.*
Chen, "Synthesis and Spectroscopic Characterization of an Alkoxysilane Dye Containing Azo-Benzothiazole Chromophore for Nonlinear Optical Applications", Dyes and Pigments, 2007, vol. 73, pp. 338-343.
Cojocariu, "Synthesis and Optical Storage Properties of a Novel Polymethacrylate with Benzothiazole Azo Chromophore in the Side Chain", Journal of Materials Chemistry, 2004, vol. 14, pp. 2909-2916. Eng.
(Continued)

*Primary Examiner* — Maureen Wallenhorst

(57) ABSTRACT

A compound represented by formula: is disclosed. R is hydrogen or alkyl; X is alkylene; Y is a bond, ether, thioether, amine, amide, ester, thioester, carbonate, thiocarbonate, carbamate, thiocarbamate, urea, thiourea, alkylene, arylalkylene, alkylarylene, or arylene, wherein alkylene, arylalkylene, alkylarylene, and arylene are optionally at least one of interrupted or terminated by at least one of an ether, thioether, amine, amide, ester, thioester, carbonate, thiocarbonate, carbamate, thiocarbamate, urea, or thiourea; and Z is an acrylate, a methacrylate, an acrylamide, a methacrylamide, a styrenyl, or a terminal alkenylene having at least three carbon atoms. A composition including the compound, and a method of determining the degree of cure of a curable polymeric resin are also disclosed.

(I)

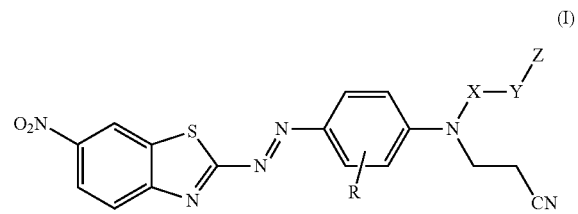

20 Claims, No Drawings

(51) Int. Cl.
| | | |
|---|---|---|
| C08K 3/38 | (2006.01) | |
| C08L 33/04 | (2006.01) | |
| C08L 41/00 | (2006.01) | |
| C09B 29/00 | (2006.01) | |
| C09B 29/033 | (2006.01) | |
| C09B 29/09 | (2006.01) | |
| C09B 67/20 | (2006.01) | |
| C09B 43/26 | (2006.01) | |
| C09B 43/28 | (2006.01) | |
| C09B 69/10 | (2006.01) | |

(56) References Cited

U.S. PATENT DOCUMENTS

| | | | |
|---|---|---|---|
| 3,382,296 A | | 5/1968 | Tenquist |
| 3,390,121 A | | 6/1968 | Burford |
| 3,773,706 A | | 11/1973 | Dunn, Jr. |
| 4,160,064 A | * | 7/1979 | Nodiff .................. C08G 59/18 428/207 |
| 4,164,492 A | | 8/1979 | Cooper |
| 4,232,136 A | | 11/1980 | Kovacsay |
| 4,241,166 A | | 12/1980 | Klupfel |
| 4,370,428 A | | 1/1983 | Danville |
| 4,440,681 A | * | 4/1984 | Tappe .................. C09B 31/043 534/640 |
| 4,460,719 A | | 7/1984 | Danville |
| 4,467,079 A | | 8/1984 | Hechenberger |
| 4,488,992 A | | 12/1984 | Yoshinaga |
| 4,507,407 A | | 3/1985 | Kluger |
| 4,522,963 A | | 6/1985 | Kecskemethy |
| 4,980,414 A | | 12/1990 | Naton |
| 5,028,456 A | | 7/1991 | Naton |
| 5,302,627 A | | 4/1994 | Field |
| 5,373,036 A | | 12/1994 | Parish |
| 5,387,488 A | | 2/1995 | Kaneko |
| 5,456,947 A | | 10/1995 | Parish |
| 5,933,559 A | | 8/1999 | Petisce |
| 5,958,584 A | * | 9/1999 | Petisce .................. C03C 25/10 385/115 |
| 6,063,864 A | | 5/2000 | Mathur |
| 6,162,842 A | * | 12/2000 | Freche .................. C09D 4/00 522/102 |
| 6,444,725 B1 | | 9/2002 | Trom |
| 6,518,356 B1 | | 2/2003 | Friese |
| 7,691,557 B2 | | 4/2010 | Bachmann |
| 7,871,446 B2 | | 1/2011 | Jordan |
| 2003/0027903 A1 | | 2/2003 | Nwoko |
| 2003/0065069 A1 | | 4/2003 | Wojciak |
| 2003/0139488 A1 | | 7/2003 | Wojciak |
| 2003/0181546 A1 | * | 9/2003 | Hettich .................. C04B 40/065 524/2 |
| 2006/0202158 A1 | * | 9/2006 | Chen .................. C09B 67/0079 252/186.1 |
| 2007/0021526 A1 | | 1/2007 | He |
| 2010/0311184 A1 | | 12/2010 | Diwu |
| 2012/0040103 A1 | | 2/2012 | Keledjian |
| 2016/0319105 A1 | | 11/2016 | Schulz |
| 2016/0319106 A1 | | 11/2016 | Ye |

FOREIGN PATENT DOCUMENTS

| | | |
|---|---|---|
| DE | 206006 | 1/1984 |
| EP | 1095985 | 5/2001 |
| EP | 1308477 | 10/2002 |
| JP | 50-69381 | 6/1975 |
| JP | 59-120612 | 7/1984 |
| JP | 61-200170 | 4/1986 |
| JP | 62-034958 | 2/1987 |
| JP | H10-237335 | 8/1998 |
| JP | 2001-131436 | 5/2001 |
| JP | 2008-144103 | 6/2008 |
| WO | 95-19379 | 7/1995 |

OTHER PUBLICATIONS

Peters, "Disperse Dyes: 4-Hetarylazo Derivatives from N-β-Cyanoethyl-N-β-Hydroxyethylaniline", Journal Chemical Technology Biotechnology 1992, vol. 53, pp. 301-308.

Peters, "Monoazo Disperse Dye Derived from Nitro-2-Aminobenzothiazoles", Dyes and Pigments, 1995, vol. 28, pp. 151-164.

Peters, "New Dyes and their Intermediates for Synthetic-polymer Fibres III-Halogenobenzothiazolylazo Dyes", Journal of the Society of Dyers and Colourists, 1969, vol. 85, No. 11, pp. 507-509.

Sanchez, "Applications of advanced hybrid organic-inorganic nanomaterials: from laboratory to market", Chemical Society Reviews, 2011, vol. 40, pp. 696-753.

Towns, "Developments in azo disperse dyes derived from heterocyclic diazo components", Dyes and Pigments, 1999, vol. 42, pp. 3-28.

International Search Report for PCT International Application No. PCT/US2014/026289, mailed on Jun. 6, 2014, 4 pages.

* cited by examiner

BENZOTHIAZOL-2-YLAZO-PHENYL COMPOUND AS DYE, COMPOSITIONS INCLUDING THE DYE, AND METHOD OF DETERMINING DEGREE OF CURE OF SUCH COMPOSITIONS

CROSS-REFERENCE TO RELATED APPLICATION

This application is a national stage filing under 35 U.S.C. 371 of PCT/US2014/026289, filed Mar. 13, 2014, which claims priority to U.S. Provisional Application No. 61/793,001, filed Mar. 15, 2013, the disclosure of which is incorporated by reference in its entirety herein.

BACKGROUND

Inclusion of a dye in a curative or catalyst composition can be useful, for example, when the curative or catalyst must be admixed with a curable resin before placement and curing the resin. The dye can be useful, for example, for indicating that the curative or catalyst is uniformly mixed with the curable resin. Peroxide and dye formulations in which the color disappears when the peroxide is used to generate radicals during the cure of a curable resin are also known. See, for example, Japanese Pat. Appl. Kokai No. SHO 59-120612, published Jul. 21, 1984, and U.S. Pat. Appl. Pub. No. 2006/0202158 (Chen et al.). Although there are many ways to determine the extent of cure in cured systems, most methods require sampling and subsequent analysis of that sample using any of a number of techniques (e.g., spectroscopy, chromatography, and rheological measurements). These methods require equipment and may require interruption of a process since many of these methods cannot be performed while a manufacturing process is taking place. In addition, many of the analysis methods require a skilled user capable of interpreting results. Formulations including a dye and a catalyst or curative in which the color disappears upon curing provide a visual indication of cure, which does not require equipment or extensive interpretation.

SUMMARY

The present disclosure provides a dye compound that can be covalently incorporated into a cured composition. In particular, the dye compound can be incorporated into a composition that cures by free-radical initiated addition polymerization. The covalent incorporation of the dye compound eliminates the potential for dye components to bloom or leech out of the cured system. Although for some compounds, modification of the dye structure can greatly alter the dye properties, we have found for the compounds disclosed herein, the covalent incorporation can be carried out without destroying the ability of the dye to become colorless upon curing.

In one aspect, the present disclosure provides a compound represented by formula:

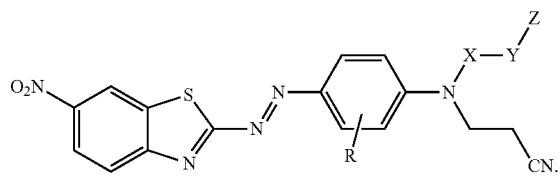

In this formula, R is hydrogen or alkyl; X is alkylene; Y is a bond, ether, thioether, amine, amide, ester, thioester, carbonate, thiocarbonate, carbamate, thiocarbamate, urea, thiourea, alkylene, arylalkylene, alkylarylene, or arylene, wherein alkylene, arylalkylene, alkylarylene, and arylene are optionally at least one of interrupted or terminated by at least one of an ether, thioether, amine, amide, ester, thioester, carbonate, thiocarbonate, carbamate, thiocarbamate, urea, or thiourea; and Z is an acrylate, a methacrylate, an acrylamide, a methacrylamide, a styrenyl, or a terminal alkenyl having at least three carbon atoms.

In another aspect, the present disclosure provides a composition comprising the compound disclosed herein, a free radical initiator, and a diluent.

In another aspect, the present disclosure provides a composition comprising a compound disclosed herein and a curable polymeric resin.

In another aspect, the present disclosure provides a method for determining degree of cure of a curable polymeric resin. The method includes providing a composition comprising a curable polymeric resin, a free-radical initiator, and a compound of claim 1 in an amount sufficient to provide the composition with a first absorbance at a wavelength in a range from 400 nanometers to 700 nanometers; and allowing the composition to cure to provide a cured composition, wherein the cured composition has a second absorbance at the wavelength that is different from the first absorbance.

In this application:

Terms such as "a", "an" and "the" are not intended to refer to only a singular entity, but include the general class of which a specific example may be used for illustration. The terms "a", "an", and "the" are used interchangeably with the term "at least one".

The phrase "comprises at least one of" followed by a list refers to comprising any one of the items in the list and any combination of two or more items in the list. The phrase "at least one of" followed by a list refers to any one of the items in the list or any combination of two or more items in the list.

The terms "cure" and "curable" refer to joining polymer chains together by covalent chemical bonds, usually via crosslinking molecules or groups, to form a network polymer. Therefore, in this disclosure the terms "cured" and "crosslinked" may be used interchangeably. A cured or crosslinked polymer is generally characterized by insolubility, but may be swellable in the presence of an appropriate solvent.

The term "polymer or polymeric" will be understood to include polymers, copolymers (e.g., polymers formed using two or more different monomers), oligomers or monomers that can form polymers, and combinations thereof, as well as polymers, oligomers, monomers, or copolymers that can be blended.

"Alkyl group" and the prefix "alk-" are inclusive of both straight chain and branched chain groups and of cyclic groups. In some embodiments, alkyl groups have up to 30 carbons (in some embodiments, up to 20, 15, 12, 10, 8, 7, 6, or 5 carbons) unless otherwise specified. Cyclic groups can be monocyclic or polycyclic and, in some embodiments, have from 3 to 10 ring carbon atoms. Terminal "alkenyl" groups have at least 3 carbon atoms.

"Alkylene" is the multivalent (e.g., divalent or trivalent) form of the "alkyl" groups defined above.

"Arylalkylene" refers to an "alkylene" moiety to which an aryl group is attached. "Alkylarylene" refers to an "arylene" moiety to which an alkyl group is attached.

The terms "aryl" and "arylene" as used herein include carbocyclic aromatic rings or ring systems, for example, having 1, 2, or 3 rings and optionally containing at least one heteroatom (e.g., O, S, or N) in the ring optionally substituted by up to five substituents including one or more alkyl groups having up to 4 carbon atoms (e.g., methyl or ethyl), alkoxy having up to 4 carbon atoms, halo (i.e., fluoro, chloro, bromo or iodo), hydroxy, or nitro groups. Examples of aryl groups include phenyl, naphthyl, biphenyl, fluorenyl as well as furyl, thienyl, pyridyl, quinolinyl, isoquinolinyl, indolyl, isoindolyl, triazolyl, pyrrolyl, tetrazolyl, imidazolyl, pyrazolyl, oxazolyl, and thiazolyl.

Substituted styrene includes alkyl, alkenyl, alkoxy, and halogen-substituted styrene.

All numerical ranges are inclusive of their endpoints and non-integral values between the endpoints unless otherwise stated.

DETAILED DESCRIPTION

In some embodiments, the dye is represented by formula:

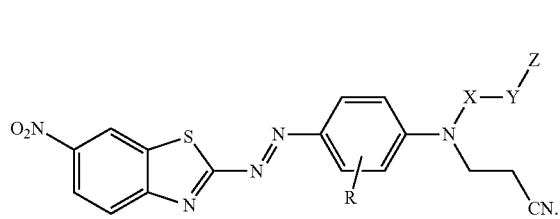

I

In formula I, R is hydrogen or alkyl. In some embodiments, R is hydrogen or alkyl having 1 to 4 carbon atoms (e.g., methyl, ethyl, n-propyl, isopropyl, n-butyl, isobutyl, or sec-butyl). In some embodiments, R is hydrogen.

In formula I, X is alkylene, in some embodiments, having from 1 to 6 or 2 to 6 carbon atoms. In some embodiments, X is —$CH_2$—$CH_2$—.

In formula I, Y is a bond, ether (i.e., —O—), thioether (i.e., —S—), amine (i.e., —$NR^1$—), amide (i.e., —$N(R^1)$—C(O)— or —C(O)—$N(R^1)$—), ester (i.e., —O—C(O)— or —C(O)—O—), thioester (i.e., —S—C(O)—, —C(O)—S—, —O—C(S)—, —C(S)—O—), carbonate (i.e., —O—C(O)—O—), thiocarbonate (i.e., —S—C(O)—O— or —O—C(O)—S—), carbamate (i.e., —$(R^1)$N—C(O)—O— or —O—C(O)—$N(R^1)$—, thiocarbamate (i.e., —$N(R^1)$—C(O)—S— or —S—C(O)—$N(R^1)$—, urea (i.e., —$(R^1)$N—C(O)—$N(R^1)$—), thiourea (i.e., —$(R^1)$N—C(S)—$N(R^1)$—), alkylene, arylalkylene, alkylarylene, or arylene, wherein alkylene, arylalkylene, alkylarylene, and arylene are optionally at least one of interrupted or terminated by at least one of an ether (i.e., —O—), thioether (i.e., —S—), amine (i.e., —$NR^1$—), amide (i.e., —$N(R^1)$—C(O)— or —C(O)—$N(R^1)$—), ester (i.e., —O—C(O)— or —C(O)—O—), thioester (i.e., —S—C(O)—, —C(O)—S—, —O—C(S)—, —C(S)—O—), carbonate (i.e., —O—C(O)—O—), thiocarbonate (i.e., —S—C(O)—O— or —O—C(O)—S—), carbamate (i.e., —$(R^1)$N—C(O)—O— or —O—C(O)—$N(R^1)$—, thiocarbamate (i.e., —$N(R^1)$—C(O)—S— or —S—C(O)—$N(R^1)$—, urea (i.e., —$(R^1)$N—C(O)—$N(R^1)$—), or thiourea (i.e., —$(R^1)$N—C(S)—$N(R^1)$—)). In any of these groups that include an $R^1$, $R^1$ is hydrogen, alkyl, aryl, arylalkylenyl, or alkylarylenyl. In some embodiments, $R^1$ is hydrogen or alkyl, for example, having 1 to 4 carbon atoms (e.g., methyl, ethyl, n-propyl, isopropyl, n-butyl, isobutyl, or sec-butyl). In some embodiments, $R^1$ is methyl or hydrogen. The phrase "interrupted by at least one functional group" refers to having part of the alkylene, arylalkylene, or alkylarylene group on either side of the functional group. An example of an alkylene interrupted by an ether is —$CH_2$—$CH_2$—O—$CH_2$—$CH_2$—. The phrase "terminated" by at least one functional group refers to a functional group bonded at one end or the other of the alkylene, arylalkylene, alkylarylene, or arylene group. The terminal functional group may either be bonded to X or Z. In some embodiments, the terminal functional group is a —O—, —O—C(O)—, —O—C(O)—O—, —O—C(O)—$NR^1$— bonded to X. In some embodiments, Y is a bond, —O—, —O—C(O)—, —O—C(O)—$NR^1$—, or alkylene optionally at least one of interrupted or terminated by at least one ether, ester, carbonate, or carbamate. In some embodiments, Y is a bond. It should be understood that when Y is a bond, Z is bonded directly to X. In other words, Y is absent from formula I. In some embodiments, Y is —O—C(O)—. In some embodiments, Y is alkylene optionally at least one of interrupted or terminated by at least one ether or ester. In these embodiments, Y may be, for example, —O—$CH_2$—$CH_2$—O—$CH_2$—$CH_2$—O—C(O)—.

In formula I, Z is a polymerizable group. It is typically a group that can undergo free-radical initiated addition polymerization. Z may be, for example, an acrylate, a methacrylate, an acrylamide, a methacrylamide, a styrenyl group, or a terminal alkenyl having at least three carbon atoms (e.g., allyl). In some embodiments, Z is acrylate, methacrylate, or styrenyl. In some embodiments, Z is acrylate or methacrylate.

Compounds of formula I can be prepared, for example, beginning with an ester represented by formula X

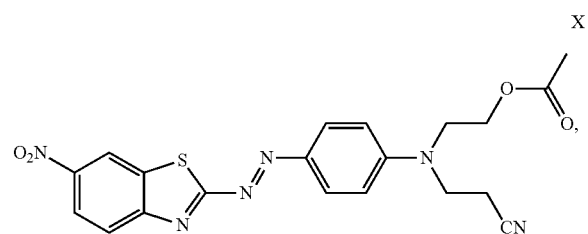 [SMILES: CC(=O)OCCN(CCC#N)c1ccc(/N=N/c2nc3ccc([N+](=O)[O-])cc3s2)cc1]

X which is commercially available, for example, from Winchem Industrial Co. Ltd, China, and China Langchem Inc., China as "DISPERSE RED 177". This compound can be hydrolyzed under known saponification conditions to provide the hydroxyl compound, shown below as formula XI. Alternatively, compounds of formula I can be prepared by treating commercially available 2-amino-6-nitrobenzothiazole with nitrosyl sulfuric acid solution prepared in situ from sodium nitrite in concentrated sulfuric acid according to the method described in Cojocariu, C., et al. *J. Mater. Chem.*, 2004, vol. 14, pages 2909-2916. The reaction can conveniently be carried out in a mixture of dichloroacetic acid and glacial acetic acid after cooling below room temperature. The resultant diazonium sulfate salt can be coupled with N-(2-cyanoethyl)-N-(2-hydroxyethyl)aniline. Other alkyl-substituted N-(2-cyanoethyl)-N-(2-hydroxyalkyl)-anilines, which can be prepared by known methods, can also be useful in the coupling reaction.

The resultant compounds of formula XI:

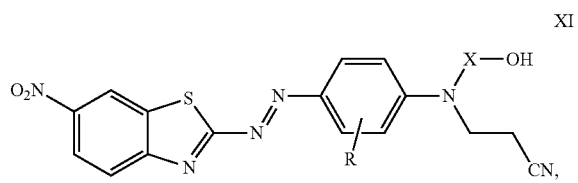

in which X and R are defined as in any of their embodiments described above, can be converted to compounds according to formula I using a variety of known synthetic methods. For example, the hydroxyl-group on the compound of formula XI can be converted to an acrylate or a methacrylate using acryloyl chloride or methacryloyl chloride, respectively, in the presence of a base to provide a compound of formula I in which Y is a bond, and Z is an acrylate or methacrylate group. Other esterification methods using acrylic acid, methacrylic acid, or equivalents thereof may be useful. The hydroxyl group in the compound of formula XI can also be reacted with a substituted or unsubstituted vinyl benzoic acid or an equivalent thereof under Mitsunobu reaction conditions to provide a compound in which Y is —O—C(O)— and Z is a styrene or substituted styrene. Conveniently the Mitsunobu coupling is carried out in the presence of triphenyl phosphine and diisopropyl azodicarboxylate or diethyl azodicarboxylate in a suitable solvent. The hydroxyl group in the compound of formula XI can also be reacted with a vinyl-substituted azlactone to provide a compound of formula I in which Y is —O—C(O)-alkylene-, and Z is an acrylamide group. The reaction can conveniently be carried out in the presence of a hindered amine. Compounds of formula XI can also be treated with isocyanatoalkyl acrylates or methacrylates or allyl isocyanate to provide compounds of formula I in which Y is a —O—C(O)—NR[1]— or a —O—C(O)—NR[1]-alkylene-, and Z is an acrylate, methacrylate, or terminal alkenyl group. Such reactions can be carried out in the presence of tin compounds (e.g., dibutyltin dilaurate) at ambient temperature. The hydroxyl group can also be converted to an amine or thiol using standard functional group manipulation. The resultant amines or mercaptans can be reacted with carboxylic acids and equivalents thereof, azlactones, and isocyanates using known chemistry to provide a variety of Y and Z groups in the compounds of formula I. Further methods for the preparation of compounds of formula I can be found in the Examples, below.

The compounds of formula I are useful in compositions, for example, including a free-radical initiator. Any free-radical initiator may be useful. In some embodiments, the free-radical initiator is an organic peroxide. Examples of useful organic peroxides include hydroperoxides (e.g., cumene, tert-butyl or tert-amyl hydroperoxide), dialkyl peroxides (e.g., di-tert-butylperoxide, dicumylperoxide, or cyclohexyl peroxide), peroxyesters (e.g., tert-butyl perbenzoate, tert-butyl peroxy-2-ethylhexanoate, tert-butyl peroxy-3,5,5-trimethylhexanoate, tert-butyl monoperoxymaleate, or di-tert-butyl peroxyphthalate), and diacylperoxides (e.g., benzoyl peroxide or lauryl peroxide). Other examples of useful organic peroxides include peroxycarbonates (e.g., tert-butylperoxy 2-ethylhexylcarbonate, tert-butylperoxy isopropyl carbonate, or di(4-tert-butylcyclohexyl) peroxydicarbonate) and ketone peroxides (e.g., methyl ethyl ketone peroxide, 1,1-di(tert-butylperoxy)cyclohexane, 1,1-di(tert-butylperoxy)-3,3,5-trimethylcyclohexane, and cyclohexanone peroxide). The organic peroxide may be selected, for example, based on the temperature desired for use of the organic peroxide and compatibility with a curable polymeric resin desired to be cured.

The free-radical initiator may also be a photoinitiator. Examples of useful photoinitiators include benzoin ethers (e.g., benzoin methyl ether or benzoin butyl ether); acetophenone derivatives (e.g., 2,2-dimethoxy-2-phenylacetophenone or 2,2-diethoxyacetophenone); 1-hydroxycyclohexyl phenyl ketone; and acylphosphine oxide derivatives and acylphosphonate derivatives (e.g., bis(2,4,6-trimethylbenzoyl)phenylphosphine oxide, diphenyl-2,4,6-trimethylbenzoylphosphine oxide, isopropoxyphenyl-2,4,6-trimethylbenzoylphosphine oxide, or dimethyl pivaloylphosphonate). Many photoinitiators are available, for example, from BASF under the trade designation "IRGACURE". The photoinitiator may be selected, for example, based on the desired wavelength for curing and compatibility with a curable polymeric resin desired to be cured.

For convenience, the compositions including the compound of formula I and the free-radical initiator may also include a diluent. The diluent can be a plasticizer, mineral spirits, water, or solvent capable of dissolving the compound of formula I (e.g., N-methyl-2-pyrrolidone, tetrahydrofuran, or ethyl acetate). The compound of formula I is suitable for addition to commercially available peroxide pastes. For example, pastes made from benzoyl peroxide, ketone peroxides (e.g., methyl ethyl ketone peroxide), hydroperoxides (e.g., cumene hydroperoxide), peroxyesters (e.g., t-butyl peroxy-2-ethylhexanoate), and diperoxyketals are all sold commercially, and a compound of formula I can be added to such pastes to provide a colored curative composition.

Compositions according to some embodiments of the present disclosure include a curable polymeric resin. Compositions including a curable polymeric resin may be combined with a compound of formula I or a composition including a compound of formula I and a free-radical initiator as described in any of the aforementioned embodiments of such compositions. Examples of useful curable polymeric resin include acrylics, epoxies, urethanes, silicones, vinyl esters, polyesters, and combinations thereof. As would be understood by a person of ordinary skill in the art, a vinyl ester is a resin produced by the esterification of an epoxy resin with an unsaturated monocarboxylic acid. The curable polymeric resin can include one or more nonreactive polymeric materials, as desired, for a particular application.

In some embodiments, compositions according to the present disclosure in any of the embodiments described above and below include the compound of formula I in an amount from 0.1 percent to 0.0001 percent by weight, based on the total weight of the curable polymeric resin and any monomer present in the composition. In some embodiments, the compound of formula I is included in the composition in an amount from 0.05 percent to 0.0005 percent, from 0.04 percent to 0.001 percent, or 0.02 percent to 0.001 percent by weight, based on the total weight of the curable polymeric resin and any monomer present in the composition.

One application of compositions according to the present disclosure that include curable polymeric resins are curable body repair materials useful in the repair of damaged vehicles and other equipment (e.g., cars, trucks, watercraft, windmill blades, aircraft, recreational vehicles, bathtubs, storage containers, and pipelines). Curable body repair materials can include two reactive components (e.g., a curable polymeric resin and catalyst or initiator) which are mixed together to form the curable body repair material. The volumetric ratio of the reactive components may be in the range of, e.g., 1:1 or higher (where higher is, e.g., 2:1, 3:1, etc.) for epoxy or urethane compounds and may be 20:1 or higher, or 25:1 or higher, or 30:1 or higher for unsaturated polyesters with a peroxide catalyst as an initiator. The curable body repair materials may include additives to enhance adhesion of the curable body material to common repair surfaces (e.g., aluminum, galvanized steel, E-coats, primers, and paints). The adhesion promoting additives may have, for example, anhydride functionality, silane functionality, or amine functionality and may or may not be covalently incorporated into the base resin.

In some embodiments, the curable polymeric resin is an unsaturated polyester resin. Unsaturated polyester resins include a polyester generally formed by a polycondensation reaction of an unsaturated dicarboxylic acid (e.g., maleic acid or fumaric acid) with a dihydroxy compound (e.g., a glycol) or diamine. Saturated dicarboxylic acids or equivalents (e.g., phthalic anhydride) can also be included. In some embodiments, the curable polymeric resin further includes at least one of styrene monomer, a substituted styrene monomer (e.g., alpha-methyl styrene, p-methyl styrene, or divinyl benzene), an acrylate monomer, a methacrylate monomer, or any compound that can be copolymerized with the unsaturated polyester resin. Illustrative curable, unsaturated polyester based compositions are described in U.S. Pat. No. 6,063,864 (Mathur et al.); U.S. Pat. No. 5,456,947 (Parish et al.); U.S. Pat. No. 4,980,414 (Naton); U.S. Pat. No. 5,028,456 (Naton); and U.S. Pat. No. 5,373,036 (Parish et al.). Other illustrative curable, unsaturated polyester based compositions are described in Int. Pat. Appl. Pub. No. WO 95/19379 (Ruggeberg).

Body filler compositions typically also include a filler. In some embodiments, the composition according to the present disclosure includes at least one of ceramic beads, polymer beads, silica, hollow ceramic elements, hollow polymeric elements, alumina, zirconia, mica, dolomite, woolasonite, fibers, talc, calcium carbonate, sodium metaborate, or clay. Such fillers, alone or in combination, can be present in a body filler in a range from 10 percent by weight to 70 percent by weight, in some embodiments, 20 percent by weight to 60 percent by weight or 40 percent by weight to 60 percent by weight, based on the total weight of the body filler composition. Silica, alumina, and zirconia, for example, can be of any desired size, including particles having an average size above 1 micrometer, between 100 nanometers and 1 micrometer, and below 100 nanometers. Silica can include nanosilica and amorphous fumed silica, for example. The term "ceramic" refers to glasses, crystalline ceramics, glass-ceramics, and combinations thereof. Hollow ceramic elements can include hollow spheres and spheroids. Examples of commercially available materials suitable for use as the hollow, ceramic elements include glass bubbles marketed by 3M Company, Saint Paul, Minn., as "3M GLASS BUBBLES" in grades K1, K15, K20, K25, K37, K46, S15, S22, S32, S35, S38, S38HS, S38XHS, S42HS, S42XHS, S60, S60HS, iM30K, iM16K, XLD3000, XLD6000, and G-65, and any of the HGS series of "3M GLASS BUBBLES"; glass bubbles marketed by Potters Industries, Carlstadt, N.J., under the trade designations "Q-CEL HOLLOW SPHERES" (e.g., grades 30, 6014, 6019, 6028, 6036, 6042, 6048, 5019, 5023, and 5028); and hollow glass particles marketed by Silbrico Corp., Hodgkins, Ill. under the trade designation "SIL-CELL" (e.g., grades SIL 35/34, SIL-32, SIL-42, and SIL-43). The hollow, ceramic elements may also be made from ceramics such as alpha-alumina, zirconia, and alumina silicates. In some embodiments, the discrete, hollow, ceramic elements are aluminosilicate microspheres extracted from pulverized fuel ash collected from coal-fired power stations (i.e., cenospheres). Useful cenospheres include those marketed by Sphere One, Inc., Chattanooga, Tenn., under the trade designation "EXTENDOSPHERES HOLLLOW SPHERES" (e.g., grades SG, MG, CG, TG, HA, SLG, SL-150, 300/600, 350 and FM-1). Other useful hollow, ceramic spheroids include silica-alumina ceramic hollow spheres with thick walls marketed by Valentine Chemicals of Lockport, La., as ZEEOSPHERES CERAMIC MICROSPHERES in grades N-200, N-200PC, N-400, N-600, N-800, N1000, and N1200. The hollow ceramic elements may have one of a variety of useful sizes but typically has a maximum dimension, or average diameter, of less than 10 millimeters (mm), more typically less than one mm. In some embodiments, the hollow ceramic elements have a maximum dimension in a range from 0.1 micrometer to one mm, from one micrometer to 500 micrometers, from one micrometer to 300 micrometers, or even from one micrometer to 100 micrometers. The mean particle size of the hollow, ceramic elements may be, for example, in a range from 5 to 250 micrometers (in some embodiments from 10 to 110 micrometers, from 10 to 70 micrometers, or even from 20 to 40 micrometers). As used herein, the term size is considered to be equivalent with the diameter and height, for example, of glass bubbles.

For repairing an automobile, for example, a technician typically mixes the two reactive components and then uses a squeegee to spread the repair compound onto the surface of the vehicle to roughly match the contour of the surface. As the curable polymeric resin reacts with the curative or initiator, it hardens to a state where it can be shaped to match the contour of the vehicle before it was damaged. During this hardening process, the filling compound typically transitions from a state of soft, gelled material to a state of moderately hard material that is relatively easy to shape with an abrasive article (e.g., sandpaper) to a state of hard material. In some embodiments, the filling compound is a filled unsaturated polyester resin that is mixed with a peroxide to facilitate cross-linking at room temperature.

The process of repairing dents using body filler can present challenges. Body filler typically requires handling in a relatively narrow time window. Premature sanding of body filler before it has reached a critical amount of cure results in sandpaper becoming plugged reducing its effectiveness, the surface of the filler becoming rough, and sometimes the filler peeling away from the surface of the vehicle. If this situation occurs, then typically the body filler has to be partially removed (usually by sanding) such that another layer of body filler can be put on top and properly shaped. Waiting too long before shaping the body filler can lengthen the time required to repair the dent as the body filler becomes hardened to a point where the material can be difficult to shape. Most body filler systems are now formulated to cure to a good shaping state in a relatively short amount of time (e.g., 4 to 12 minutes). Identifying the time period when the filling compound has transitioned into the state where it is relatively easy to shape is important to speed up that part of the repair process.

Other processes that may be enhanced by recognizing the extent of cure in a curable composition include curing medical adhesives and dental composites or adhesives. In some of these applications, the curable composition includes a photoinitiator. In some embodiments, these compositions include acrylate, methacrylate, acrylamide, or methacrylamide monomers in combination with oligomeric urethane acrylates or methacrylate or other functional oligomers.

In compositions that are light cured, the compositions according to the present disclosure also provide the advantage that they can indicate when they have been exposed to a curing light. In these cases, the disappearance or muting of the color can indicate that the compositions have been exposed to the curing light. The color change in the presently disclosed compositions indicates that free radicals have been generated, which may distinguish these compositions from those that undergo photobleaching. This feature can be beneficial when a manufacturing line has been stopped, for example, so that operators can easily differentiate exposed and unexposed compositions.

In some embodiments, compositions according to the present disclosure include a compound of formula I and one or more monomers (e.g., styrene, a substituted styrene, acrylate, methacrylate, acrylamide, or methacrylamide monomers). In some of these embodiments, the composition further includes a free-radical initiator.

The compounds of formula I according to the present disclosure can be useful for indicating the extent of cure in the applications described above. The compounds of formula I changes color in the presence of free-radicals, and thus can directly indicate cure by correlation of the concentration of free-radicals in the system. Compounds of formula I have an initial colored state and a less colored or colorless final state, as demonstrated in the examples, below. For many applications, such as auto repair or dental applications, a colorless or nearly colorless final state is highly desirable. In auto repair, a cure indicator that retains a specific color in its cured state can be problematic when it comes to painting. Furthermore, the compounds according to the present disclosure are covalently bound into the curable polymeric resin and advantageously do not migrate out of the cured system over time.

Accordingly, the present disclosure also provides a method for determining degree of cure of a curable composition, including any of the curable compositions described above. In some embodiments, the method includes providing a composition comprising a curable polymeric resin, a free-radical initiator, and a compound of formula I in an amount sufficient to provide the composition with a first absorbance at a wavelength in a range from 400 nanometers to 700 nanometers. The wavelength may in a range, for example, from 450 nanometers to 650 nanometers, typically in a range from 500 nanometers to 550 nanometers. Allowing the composition to cure or curing the composition provides a cured composition that has a second absorbance at the wavelength that is different from the first absorbance. In some embodiments, the absorbance at the selected wavelength is decreased by at least 20, 25, 30, 35, 40, 45, or 50 percent or more. The initial and final absorbance can be measured, for example, using a UV/VIS spectrometer or a colorimeter. A composition having an absorbance at a wavelength in a range from 400 nanometers to 700 nanometers would typically be perceived by the human eye as a particular color. In some embodiments, a color in the composition is no longer visible in the cured composition. In these embodiments, a difference between the second absorbance and the first absorbance is visually determined. In some embodiments, providing the composition includes mixing the curable polymeric resin with a curative comprising the free-radical initiator and the compound of formula I. The free-radical initiator may be any of those described above, and the curative may also include any of the diluents described above. Advantageously, mixing can be carried out until the visible color is uniformly dispersed in the composition.

The properties provided by the compounds of formula I are unexpected in view of other potential compounds that were not successfully covalently incorporated into a curable resin system while maintaining color loss properties upon curing. For example, the azo-2-naphthol dye Sudan III was modified by placing an acrylate group on the hydroxyl group of the compound. The addition of Sudan III to 3M Premium Body Filler (3M part number 50597) and then subsequent curing showed the initial pink color disappeared around 6 minutes. However, when the Sudan III was converted into an acrylate as described in Illustrative Example A, no fading of the initial color was observed upon cure. In both cases, the body filler cured the same as when no dye was present. It is believed, the mechanism by which this dye goes colorless was disrupted by covalently incorporating the polymerizable group into the dye.

Also, a solution of the acetyl functional para-nitrophenyl dye, 4-(4-nitrophenylazo)-N-(2-cyanoethyl)-N-(acetoxyethyl)aniline, similar to compounds prepared in Japanese Pat. Appl. Kokai No. SHO 59-120612, published Jul. 21, 1984, was prepared in Illustrative Example B and was evaluated in a body filler composition. Although the body filler cured properly, very little or no discernible color change was observed.

Some Embodiments of the Disclosure

In a first embodiment, the present disclosure provides a compound represented by formula:

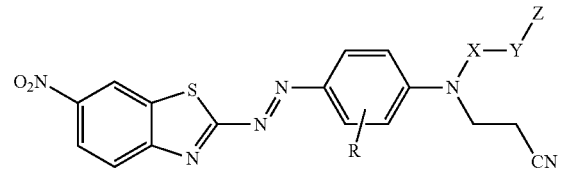

wherein

R is hydrogen or alkyl;

X is alkylene;

Y is a bond, ether, thioether, amine, amide, ester, thioester, carbonate, thiocarbonate, carbamate, thiocarbamate, urea, thiourea, alkylene, arylalkylene, alkylarylene, or arylene, wherein alkylene, arylalkylene, alkylarylene, and arylene are optionally at least one of interrupted or terminated by at least one of an ether, thioether, amine, amide, ester, thioester, carbonate, thiocarbonate, carbamate, thiocarbamate, urea, or thiourea; and Z is an acrylate, a methacrylate, an acrylamide, a methacrylamide, a styrenyl, or a terminal alkenylene having at least three carbon atoms.

In a second embodiment, the present disclosure provides the compound of the first embodiment, wherein R is hydrogen.

In a third embodiment, the present disclosure provides the compound of the first or second embodiment, wherein Z is acrylate, methacrylate, or styrenyl.

In a fourth embodiment, the present disclosure provides the compound of any one of the first to third embodiments, wherein Y is a bond, —O—, —O—C(O)—, —O—C(O)—NR$^1$—, or alkylene optionally at least one of interrupted or terminated by at least one ether, ester, carbonate, or carbamate, and wherein R$^1$ is hydrogen, alkyl, aryl, alkylarylenyl, or arylalkylenyl.

In a fifth embodiment, the present disclosure provides the compound of any one of the first to fourth embodiments, wherein Y is a bond, —O—C(O)—, or alkylene optionally at least one of interrupted or terminated by at least one ether or ester.

In a sixth embodiment, the present disclosure provides the compound of any one of the first to fifth embodiments, wherein —X—Y—Z is —CH$_2$CH$_2$—O—C(O)—CH=CH$_2$, —CH$_2$CH$_2$—O—C(O)—C(CH$_3$)=CH$_2$, or —CH$_2$CH$_2$—O—C(O)—C$_6$H$_4$—CH=CH$_2$.

In a seventh embodiment, the present disclosure provides a composition comprising the compound of any one of the first to sixth embodiments, a free radical initiator, and a diluent.

In an eighth embodiment, the present disclosure provides the composition of the seventh embodiment, wherein the free-radical initiator is an organic peroxide.

In a ninth embodiment, the present disclosure provides the composition of the seventh embodiment, wherein the free-radical initiator is a photoinitiator.

In a tenth embodiment, the present disclosure provides the composition any one of the seventh to ninth embodiments, further comprising a curable polymeric resin.

In an eleventh embodiment, the present disclosure provides a composition comprising the compound of any one of the first to sixth and at least one of a curable polymeric resin or curable monomer.

In a twelfth embodiment, the present disclosure provides the composition of the tenth or eleventh embodiment, wherein the curable polymeric resin is an unsaturated polyester resin.

In a thirteenth embodiment, the present disclosure provides the composition of the tenth or eleventh embodiment, wherein the curable polymeric resin is a vinyl ester resin.

In a fourteenth embodiment, the present disclosure provides the composition any one of the tenth to thirteenth embodiments, further comprising at least one of styrene monomer, a substituted styrene monomer, an acrylate monomer, a methacrylate monomer, or an acrylamide or methacrylamide monomer.

In a fifteenth embodiment, the present disclosure provides the composition of any one of the tenth to fourteenth embodiments, further comprising at least one of ceramic beads, polymer beads, silica, hollow ceramic elements, hollow polymeric elements, alumina, zirconia, mica, dolomite, woolasonite, fibers, talc, calcium carbonate, sodium metaborate, or clay.

In a sixteenth embodiment, the present disclosure provides a method for determining degree of cure of a curable polymeric resin or indicating curing in a curable polymeric resin, the method comprising:

providing a composition comprising a curable polymeric resin, a free-radical initiator, and a compound of any one of the first to sixth embodiments in an amount sufficient to provide the composition with a first absorbance at a wavelength in a range from 400 nanometers to 700 nanometers; and allowing the composition to cure to provide a cured composition, wherein the cured composition has a second absorbance at the wavelength that is different from the first absorbance.

In a seventeenth embodiment, the present disclosure provides the method of the sixteenth embodiment, wherein the difference between the first absorbance and the second absorbance is visually determined.

In an eighteenth embodiment, the present disclosure provides the method of the sixteenth or seventeenth embodiment, wherein providing the composition comprises mixing the curable polymeric resin with a curative comprising the free-radical initiator and the compound.

In a nineteenth embodiment, the present disclosure provides the method of the sixteenth or seventeenth embodiment, wherein providing the composition comprises mixing the curable polymeric resin and the compound and then combining the free-radical initiator.

In a twentieth embodiment, the present disclosure provides the method of the eighteenth or nineteenth embodiment, wherein mixing is carried out until the composition is uniformly colored.

In a twenty-first embodiment, the present disclosure provides the method of any one of the sixteenth to twentieth embodiments, wherein the curable polymeric resin is an unsaturated polyester resin or a vinyl ester resin.

In twenty-second embodiment, the present disclosure provides the method of any one of the sixteenth to twenty-first embodiments, wherein the composition further comprises at least one of styrene monomer, a substituted styrene monomer, an acrylate monomer, a methacrylate monomer, an acrylamide monomer, or a methacrylamide monomer.

In a twenty-third embodiment, the present disclosure provides a method for determining degree of cure of a curable composition or indicating curing in a curable composition, the method comprising:

providing a composition comprising a curable monomer, a free-radical initiator, and a compound of any one of the first to sixth embodiments in an amount sufficient to provide the composition with a first absorbance at a wavelength in a range from 400 nanometers to 700 nanometers; and allowing the composition to cure to provide a cured composition, wherein the cured composition has a second absorbance at the wavelength that is different from the first absorbance.

In a twenty-fourth embodiment, the present disclosure provides the method of the twenty-third embodiment, wherein the curable monomer comprises at least one of styrene monomer, a substituted styrene monomer, an acrylate monomer, a methacrylate monomer, an acrylamide monomer, or a methacrylamide monomer.

In a twenty-fifth embodiment, the present disclosure provides the method of any one of the sixteenth to twenty-fourth embodiments, wherein the free-radical initiator is an organic peroxide.

In a twenty-sixth embodiment, the present disclosure provides the method of any one of the sixteenth to twenty-fifth embodiments, wherein the free-radical initiator is a photoinitiator.

In a twenty-seventh embodiment, the present disclosure provides the method of any one of the sixteenth to twenty-sixth embodiments, wherein the composition further comprises at least one of ceramic beads, polymer beads, silica, hollow ceramic elements, hollow polymeric elements, alumina, zirconia, mica, dolomite, woolasonite, fibers, talc, calcium carbonate, sodium metaborate, or clay.

In a twenty-eighth embodiment, the present disclosure provides a compound represented by formula:

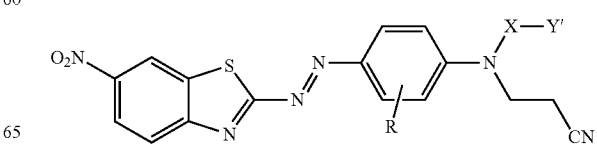

wherein

R is hydrogen or alkyl;

X is alkylene;

Y' is an amine or thiol.

In order that this disclosure can be more fully understood, the following examples are set forth. It should be understood that these examples are for illustrative purposes only, and are not to be construed as limiting this disclosure in any manner.

EXAMPLES

Reagents

Vinyl dimethylazlactone was obtained from IsoChem S.A.S., Evry, France. All other reagents were obtained, or are available from fine chemical vendors, such as: Sigma-Aldrich Company, St. Louis, Mo.; EMD Millipore Chemicals, Billerica, Mass.; Alfa Aesar, Ward Hill, Mass.; J. T. Baker, Phillipsburg, N.J.; BDH Merck Ltd., Poole, Dorset, UK, and Cambridge Isotope Laboratories, Inc., Andover, Mass.; or may be synthesized by known methods. Unless otherwise reported, all ratios are by weight.

The following abbreviations are used to describe the examples:

° C.: degrees Centigrade
cm: centimeter
CDCl$_3$: deuterated chloroform
d$_6$-DMSO: deuterated dimethyl sulfoxide
mg: milligram
mil: 10$^{-3}$ inch
mL: milliliter
mm: millimeter
mmol: millimole
μL: microliter
μmol: micromole
nm: nanometer
NMR: nuclear magnetic resonance
Pa: Pascal Synthesis of 3-{(2-hydroxy-ethyl)-[4-(6-nitro-benzothiazol-2-ylazo)-phenyl]-amino}-propionitrile 5.00 grams (25.6 mmol) 2-amino-6-nitrobenzothiazole was added to 66 mL of a 5:1 (by volume) solution of dichloroacetic acid:glacial acetic acid in a 250 mL flask and dissolved by heating to 50° C. for 15 minutes. The solution was cooled to 0° C., then slowly added, with constant stirring over a 10 minute period, to a 250 mL flask containing a solution of 1.94 grams (28.1 mmol) sodium nitrite in 13 mL concentrated sulfuric acid held at 0° C. After stirring for an additional 30 minutes, this solution was slowly added to a 250 mL flask containing a mixture of 4.20 grams (22.1 mmol) N-(2-cyanoethyl)-N-(2-hydroxyethyl)aniline in 13 mL acetic acid, also held at 0° C., and stirred for 1 hour. The reaction mixture was then neutralized by the addition of a saturated aqueous sodium carbonate solution until the pH of the reaction mixture was approximately 7, and the resulting precipitate isolated by vacuum filtration. The precipitate was dissolved in 200 mL methylene chloride, then dried by passing through a bed of anhydrous sodium sulfate, filtered, and condensed in a rotary evaporator. The resulting solid was further purified by loading onto a 3 by 23 cm silica gel column, then eluting with an acetone:methylene chloride solution where the solvent ratio, by volume, was gradually changed from 10:90 to 30:70. Subsequent fractions containing the pure compound were combined, condensed under reduced pressure and then dried under a vacuum of 0.3 mm mercury (40.0 Pa) at approximately 21° C. to yield 4.30 grams of a purple solid, subsequently confirmed by NMR spectroscopy to be 3-{(2-hydroxy-ethyl)-[4-(6-nitro-benzothiazol-2-ylazo)-phenyl]-amino}-propionitrile [$^1$H NMR (500 MHz, d$_6$-DMSO) δ 9.07 (d, J=2.4 Hz, 1H), 8.32 (dd, J=2.4, 8.9 Hz, 1H), 8.17 (d, J=8.9 Hz, 1H), 7.91 (d, J=9.4 Hz, 2H), 7.11 (d, J=9.4 Hz, 2H), 4.99 (t, J=5.1 Hz, 1H), 3.95 (t, J=7.1 Hz, 2H), 3.69 (m, 4H), 2.91 (t, J=6.9 Hz, 2H)].

Compound Example 1

Synthesis of 2-methyl-acrylic acid 2-{(2-cyano-ethyl)-[4-(6-nitro-benzothiazol-2-ylazo)-phenyl]-amino}-ethyl ester

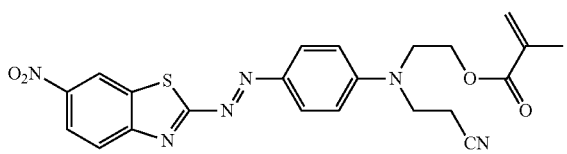 [SMILES: C=C(C)C(=O)OCCN(CCC#N)c1ccc(/N=N/c2nc3ccc([N+](=O)[O-])cc3s2)cc1]

0.29 mL (2.1 mmol) triethylamine was added to a 50 mL flask containing a solution of 0.55 grams (1.39 mmol) 3-{(2-hydroxy-ethyl)-[4-(6-nitro-benzothiazol-2-ylazo)-phenyl]-amino}-propionitrile in 20 mL tetrahydrofuran at approximately 21° C., after which it was cooled to 0° C. 162 μL (1.67 mmol) methacryloyl chloride was then added, and the mixture stirred under an atmosphere of nitrogen for 16 hours while the temperature was maintained at 0° C. The reaction mixture was filtered, and the filtrate condensed in a rotary evaporator. The resulting purple material was dissolved in chloroform, washed twice with a saturated sodium carbonate solution, washed twice with deionized water and washed once with a saturated sodium chloride solution. The organic portion was then dried by passing through a bed of anhydrous sodium sulfate, filtered, and condensed in a rotary evaporator. The resulting solid was further purified by loading onto an 3 by 23 cm silica gel column, then eluting with a methyl tert-butyl ether:methylene chloride solution where the solvent ratio, by volume, was gradually changed from 4:96 to 10:90. Subsequent fractions containing the pure compound were combined, condensed under reduced pressure and then dried under a vacuum of 0.3 mm mercury (40.0 Pa) at approximately 21° C. to yield 190 mg of a solid subsequently confirmed by NMR spectroscopy to be 2-methyl-acrylic acid 2-{(2-cyano-ethyl)-[4-(6-nitro-benzothiazol-2-ylazo)-phenyl]-amino}-ethyl ester [$^1$H NMR (500 MHz, CDCl$_3$) δ 8.84 (d, J=2.3 Hz, 1H), 8.40 (dd, J=2.3, 9.0 Hz, 1H), 8.23 (d, J=9.0 Hz, 1H), 8.11 (d, J=9.3 Hz, 2H), 6.93 (d, J=9.4 Hz, 2H), 6.15 (m, 1H), 5.68 (m, 1H), 4.49 (t, J=5.9 Hz, 2H), 3.98 (m, 4H), 2.82 (t, J=6.9 Hz, 2H), 1.99 (m, 3H)].

Compound Example 2

Synthesis of acrylic acid 2-{(2-cyano-ethyl)-[4-(6-nitro-benzothiazol-2-ylazo)-phenyl]-amino}-ethyl ester

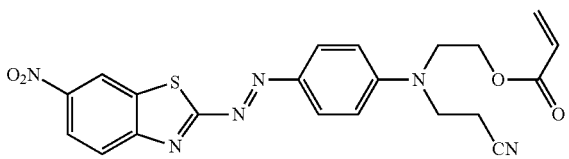 [SMILES: C=CC(=O)OCCN(CCC#N)c1ccc(/N=N/c2nc3ccc([N+](=O)[O-])cc3s2)cc1]

422 μL (3.03 mmol) triethylamine was added to a 100 mL flask containing a solution of 0.399 grams (1.01 mmol) 3-{(2-hydroxy-ethyl)-[4-(6-nitro-benzothiazol-2-ylazo)-phenyl]-amino}-propionitrile in 20 mL N,N-dimethyl formamide at approximately 21° C. This solution was stirred under an atmosphere of nitrogen for 10 minutes at approximately 21° C. 195 μL (2.41 mmol) acryloyl chloride was then added. The flask was placed in an oil bath, and the mixture was stirred under an atmosphere of nitrogen for 18 hours while the temperature was maintained at approximately 70° C. The reaction mixture was then partitioned between water (approximately 50 mL) and methylene chloride (approximately 50 mL). The aqueous layer was made basic by adding 5 mL of a saturated aqueous sodium bicarbonate solution. The organic layer was then removed, and the aqueous layer was extracted twice more with methylene chloride (approximately 50 mL each time). The organic layers were combined, dried by passing through a bed of anhydrous sodium sulfate, filtered, and condensed in a rotary evaporator. The resulting solid was further purified by loading onto an 4 by 30 cm silica gel column, then eluting with an approximately 5:95 (by volume) ethyl acetate:methylene chloride solution. Subsequent fractions containing the pure compound were combined, condensed under reduced pressure and then dried under a vacuum of 0.3 mm mercury (40.0 Pa) at approximately 21° C. to yield 280 mg of a solid subsequently confirmed by NMR spectroscopy to be acrylic acid 2-{(2-cyano-ethyl)-[4-(6-nitro-benzothiazol-2-ylazo)-phenyl]amino}-ethyl ester [$^1$H NMR (500 MHz, CDCl$_3$) δ 8.78 (d, J=2.2 Hz, 1H), 8.34 (dd, J=2.2, 8.9 Hz, 1H), 8.17 (d, J=8.9 Hz, 1H), 8.06 (m, 2H), 6.86 (m, 2H), 6.42 (dd, J=1.2, 17.3 Hz, 1H), 6.11 (dd, J=10.5, 17.3 Hz, 1H), 5.89 (dd, J=1.2, 10.5 Hz, 1H), 4.43 (t, J=5.8 Hz, 2H), 3.91 (t, J=6.8 Hz, 2H), 3.90 (t, J=5.8 Hz, 2H), 2.75 (t, J=6.8 Hz, 2H)].

Compound Example 3

Synthesis of 2-acryloylamino-2-methyl-propionic acid 2-{(2-cyano-ethyl)-[4-(6-nitro-benzothiazol-2-ylazo)-phenyl]-amino}-ethyl ester

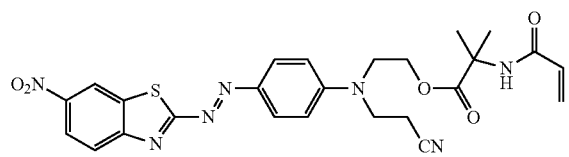 [SMILES: C=CC(=O)NC(C)(C)C(=O)OCCN(CCC#N)c1ccc(/N=N/c2nc3ccc([N+](=O)[O-])cc3s2)cc1]

540 μL (4.04 mmol) vinyl dimethylazlactone was added to a 100 mL flask containing a solution of 0.399 grams (1.01 mmol) 3-{(2-hydroxy-ethyl)-[4-(6-nitro-benzothiazol-2-ylazo)-phenyl]-amino}-propionitrile in 30 mL N,N-dimethyl formamide at approximately 21° C. 15 μL (101 μmol) 1,8-diazabicyclo[5.4.0]undec-7-ene was then added. The mixture was stirred under an atmosphere of nitrogen for 18 hours at approximately 21° C. The reaction mixture was then partitioned between water (approximately 50 mL) and methylene chloride (approximately 50 mL). The organic layer was then removed, and the aqueous layer was extracted twice more with methylene chloride (approximately 50 mL each time). The organic layers were combined, dried by passing through a bed of anhydrous sodium sulfate, filtered, condensed in a rotary evaporator, and then dried under a vacuum of 0.3 mm mercury (40.0 Pa) at approximately 21° C. to yield 465 mg of a solid subsequently confirmed by NMR spectroscopy to be 2-acryloylamino-2-methyl-propionic acid 2-{(2-cyano-ethyl)-[4-(6-nitro-benzothiazol-2-ylazo)-phenyl]-amino}-ethyl ester [$^1$H NMR (500 MHz, CDCl$_3$) δ 8.78 (d, J=2.2 Hz, 1H), 8.35 (dd, J=2.2, 8.9 Hz, 1H), 8.16 (d, J=8.9 Hz, 1H), 8.05 (m, 2H), 6.84 (m, 2H), 6.28 (dd, J=1.3, 17.0 Hz, 1H), 6.06 (dd, J=10.8, 17.0 Hz, 1H), 5.86 (s, 1H), 5.68 (dd, J=1.3, 10.8 Hz, 1H), 4.41 (t, J=5.6 Hz, 2H), 3.92 (t, J=7.0 Hz, 2H), 3.87 (t, J=5.6 Hz, 2H), 2.75 (t, J=7.0 Hz, 2H), 1.53 (s, 6H)].

Compound Example 4

Synthesis of 4-vinyl-benzoic acid 2-{(2-cyano-ethyl)-[4-(6-nitro-benzothiazol-2-ylazo)-phenyl]-amino}-ethyl ester

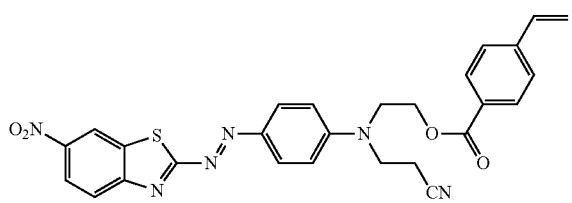 [SMILES: C=Cc1ccc(C(=O)OCCN(CCC#N)c2ccc(/N=N/c3nc4ccc([N+](=O)[O-])cc4s3)cc2)cc1]

0.199 grams (503 μmol) 3-{(2-hydroxy-ethyl)-[4-(6-nitro-benzothiazol-2-ylazo)-phenyl]-amino}-propionitrile, 57.6 mg (389 μmol) 4-vinyl benzoic acid and 0.229 grams triphenylphosphine were dissolved in 10 mL tetrahydrofuran in a 100 mL flask at approximately 21° C. This solution was cooled to 0° C. by placing the flask in an ice/water bath. The flask was equipped with an addition funnel containing a solution of 265 μL (1.35 mmol) diisopropyl azodicarboxylate (DIAD) in 5 mL of tetrahydrofuran (THF). The DIAD/THF solution was added dropwise to the stirred reaction mixture over a period of 30 minutes under an atmosphere of nitrogen while the temperature was maintained at approximately 0° C. When the addition was complete, the reaction mixture was allowed to warm to approximately 21° C. The reaction mixture was then stirred under an atmosphere of nitrogen for 18 hours at approximately 21° C. The reaction mixture was condensed in a rotary evaporator. The resulting material was partitioned between water (approximately 50 mL) and methylene chloride (approximately 50 mL). The organic layer was then removed, and the aqueous layer was extracted twice more with methylene chloride (approximately 50 mL each time). The organic layers were combined, dried by passing through a bed of anhydrous sodium sulfate, filtered, and condensed in a rotary evaporator. The resulting solid was further purified by loading onto an 4 by 20 cm silica gel column, then eluting with an approximately 5:95 (by volume) ethyl acetate:methylene chloride solution. Subsequent fractions containing the pure compound were combined, condensed under reduced pressure and then dried under a vacuum of 0.3 mm mercury (40.0 Pa) at approximately 21° C. to yield 143 mg of a solid subsequently confirmed by NMR spectroscopy to be 4-vinyl-benzoic acid 2-{(2-cyano-ethyl)-[4-(6-nitro-benzothiazol-2-ylazo)-phenyl]-amino}-ethyl ester [$^1$H NMR (500 MHz, CDCl$_3$) δ 8.71 (d, J=2.2 Hz, 1H), 8.29 (dd, J=2.2, 8.9 Hz, 1H), 8.12 (d, J=8.9 Hz, 1H), 8.00 (m, 2H), 7.92 (m, 2H), 7.44 (m, 2H), 6.88 (m, 2H), 6.71 (dd, J=10.7, 17.6 Hz, 1H), 5.85 (d, J=17.6

Hz, 1H), 5.37 (d, J=10.7 Hz, 1H), 4.57 (t, J=5.8 Hz, 2H), 3.99 (t, J=5.8 Hz, 2H), 3.93 (t, J=6.8 Hz, 2H), 2.77 (t, J=6.8 Hz, 2H)].

Compound Example 5

Synthesis of allyl-carbamic acid 2-{(2-cyano-ethyl)-[4-(6-nitro-benzothiazol-2-ylazo)-phenyl]-amino}-ethyl ester

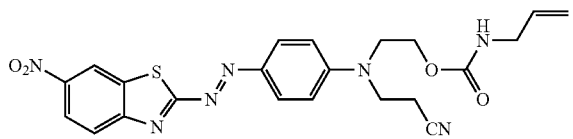 [SMILES: C=CCNC(=O)OCCN(CCC#N)c1ccc(/N=N/c2nc3ccc([N+](=O)[O-])cc3s2)cc1]

180 μL (2.04 mmol) allyl isocyanate was added to a 20 mL vial containing a solution of 0.200 grams (505 μmol) 3-{(2-hydroxy-ethyl)-[4-(6-nitro-benzothiazol-2-ylazo)-phenyl]-amino}-propionitrile in 10 mL N,N-dimethyl formamide at approximately 21° C. 30 μL (505 μmol) dibutyltin dilaurate was then added. The vial was capped and mixed in a mechanical shaker, model "WRIST ACTION SHAKER MODEL 75" from Burrell Scientific, Pittsburgh, Pa., for 18 hours at approximately 21° C. The reaction mixture was then partitioned between water (approximately 50 mL) and methylene chloride (approximately 50 mL). The organic layer was then removed, and the aqueous layer was extracted twice more with methylene chloride (approximately 50 mL each time). The organic layers were combined, dried by passing through a bed of anhydrous sodium sulfate, filtered, condensed in a rotary evaporator, and then dried under a vacuum of 1.0 mm mercury (133.3 Pa) at approximately 90° C. to yield 260 mg of a solid subsequently confirmed by NMR spectroscopy to be allyl-carbamic acid 2-{(2-cyano-ethyl)-[4-(6-nitro-benzothiazol-2-ylazo)-phenyl]-amino}-ethyl ester [$^1$H NMR (500 MHz, CDCl$_3$) δ 8.68 (d, J=2.2 Hz, 1H), 8.26 (dd, J=2.2, 9.0 Hz, 1H), 8.09 (d, J=9.0 Hz, 1H), 7.89 (m, 2H), 6.81 (m, 2H), 5.78 (m, 1H), 5.14 (d, J=17.3 Hz, 1H), 5.10 (d, J=10.2 Hz, 1H), 4.94 (t, J=5.5 Hz, 1H), 4.33 (t, J=5.6 Hz, 2H), 3.86 (t, J=6.8 Hz, 2H), 3.83 (t, J=5.6 Hz, 2H), 2.75 (t, J=6.8 Hz, 2H)].

Synthesis of acrylic acid 1-(4-phenylazo-phenylazo)-naphthalen-2-yl ester

320 μL (2.30 mmol) triethylamine was added to a 100 mL flask containing a solution of 0.200 grams 1-(4-phenylazo-phenylazo)-naphthalen-2-ol (1.01 mmol) in 25 mL at approximately 21° C. This solution was stirred under an atmosphere of nitrogen for 10 minutes at approximately 21° C. 200 μL (2.46 mmol) acryloyl chloride was then added. The flask was placed in an oil bath and the mixture was stirred under an atmosphere of nitrogen for 18 hours while the temperature was maintained at approximately 55° C. The reaction mixture was condensed in a rotary evaporator. The resulting material was then partitioned between water (approximately 50 mL) and methylene chloride (approximately 50 mL). The organic layer was then removed, and the aqueous layer was extracted twice more with methylene chloride (approximately 50 mL each time). The organic layers were combined, dried by passing through a bed of anhydrous sodium sulfate, filtered, and condensed in a rotary evaporator. The resulting solid was further purified by loading onto an 3 by 40 cm silica gel column, then eluting with an ethyl acetate:petroleum ether solution where the solvent ratio, by volume, was gradually changed from 0:100 to 20:80. Subsequent fractions containing the pure compound were combined, condensed under reduced pressure and then dried under a vacuum of 0.3 mm mercury (40.0 Pa) at approximately 21° C. to yield 96 mg of a solid subsequently confirmed by NMR spectroscopy to be acrylic acid 1-(4-phenylazo-phenylazo)-naphthalen-2-yl ester [$^1$H NMR (500 MHz, CDCl$_3$) δ 8.74 (m, 1H), 8.06 (s, 4H), 7.97 (m, 3H), 7.93 (m, 1H), 7.62 (m, 6H), 7.36 (m, 1H), 6.64 (dd, J=1.2, 17.4 Hz, 1H), 6.39 (dd, J=10.5, 17.4 Hz, 1H), 6.08 (dd, J=1.2, 10.5 Hz, 1H)].

Composition Example 1

0.33 grams of a 3 mg/mL solution of 2-methyl-acrylic acid 2-{(2-cyano-ethyl)-[4-(6-nitro-benzothiazol-2-ylazo)-phenyl]-amino}-ethyl ester in N-methyl-2-pyrrolidone was uniformly mixed with 2.0 grams of a white 50% benzoyl peroxide hardener paste, obtained under the trade designation "BENOX B-50" from Syrgis Performance Initiators, Inc., Helena, Ark. 0.46 grams of the colored hardener was then uniformly mixed on a palette for 45 seconds at 21° C. with 20.0 grams of a white automotive body filler that had been dispensed from the cartridge of a body filler kit, obtained under the trade designation "3M PREMIUM BODY FILLER, PART No. 50597" from 3M Company, St. Paul, Minn. The resulting pink material was spread out on the palette to an approximate thickness of ⅛-¼ inches (3.18-6.35 mm) After 6 minutes, a hardened white body filler was obtained with no residual pink color. Full cure was confirmed by manually sanding the white body filler, without clogging, using a 2.75 by 6-inch (7.0 by 15.2 cm) P80 grade sandpaper, trade designation "IMPERIAL GRADE P80E" obtained from 3M Company, by means of a sanding block.

Composition Example 2

15 μL of a 5 mg/mL solution of 2-methyl-acrylic acid 2-{(2-cyano-ethyl)-[4-(6-nitro-benzothiazol-2-ylazo)-phenyl]-amino}-ethyl ester in N-methyl-2-pyrrolidone was uniformly mixed with 3.0 grams of a medical grade adhesive, obtained under the trade designation "3M SCOTCH-WELD MEDICAL GRADE LIGHT CURE ADHESIVE MG90-77 UV" from 3M Company, St. Paul, Minn. A 1.2 cm diameter circle was cut in a 15 mil (0.38 mm) thick sheet of rubber. The rubber sheet with hole was placed on a glass slide, the circle was filled with the pink adhesive formulation described above and a second glass slide was placed over the rubber sheet. The construction was held together with clips. The area of the IR absorbance between 6202-6102 cm$^{-1}$ was measured of the sample prior to cure using an IR spectrometer, model "NEXUS 670 FT-IR ESP" from Thermo Fischer Scientific, Minneapolis, Minn. The absorbance at 517 nm was measured of the sample prior to cure using a spectrometer, model "CARY 60 UV/VIS" from Agilent Technologies, Santa Clara, Calif. The sample was then cured using a UV light source, model "OMNICURE 52000" from Lumen Dynamics Group, Inc., Mississauga, Ontario, Canada, fitted with a 320-500 nm filter, 3 mm fiber optic (Part No. 806-00012) and small collimating lens (Part No. 810-00016). The light guide was positioned 2 cm from the surface of the glass slide and at a slight angle so that the IR absorbance at 6202-6102 cm$^{-1}$ could be measured while curing. The sample was exposed to the light source at a power setting of 20 for 20 seconds. After 20 seconds of cure, the IR absorbance showed the sample to be at approximately 96% conversion. The sample was then placed back in the CARY 60 UV/VIS spectrometer and the absorbance of the sample at 517 nm was measured. A decrease in absorbance of 35% was observed.

Composition Example 3

200 μL of a 5.2 mg/mL solution of acrylic acid 2-{(2-cyano-ethyl)-[4-(6-nitro-benzothiazol-2-ylazo)-phenyl]-amino}-ethyl ester in N-methyl-2-pyrrolidone was uniformly mixed with 10.1 grams of the "3M PREMIUM BODY FILLER PART No. 50597" from 3M Company. The resulting body filler was pink. 0.21 grams of the "BENOX B-50" hardener was then uniformly mixed on a palette for 90 seconds at 21° C. with the pink body filler. The resulting pink material was spread out on the palette to an approximate thickness of ⅛-¼ inches (3.18-6.35 mm) After 10 minutes, a hardened white body filler was obtained with no residual pink color.

Composition Example 4

75 μL of a 5.0 mg/mL solution of 2-acryloylamino-2-methyl-propionic acid 2-{(2-cyano-ethyl)-[4-(6-nitro-benzothiazol-2-ylazo)-phenyl]amino}-ethyl ester in N-methyl-2-pyrrolidone was uniformly mixed with 10.1 grams of the "3M PREMIUM BODY FILLER PART No. 50597" from 3M Company. The resulting body filler was pink. 0.20 grams of the "BENOX B-50" hardener was then uniformly mixed on a palette for 90 seconds at 21° C. with the pink body filler. The resulting pink material was spread out on the palette to an approximate thickness of ⅛-¼ inches (3.18-6.35 mm). After 7.5 minutes, a hardened white body filler was obtained with no residual pink color.

Composition Example 5

75 μL of a 5.0 mg/mL solution of 4-vinyl-benzoic acid 2-{(2-cyano-ethyl)-[4-(6-nitro-benzothiazol-2-ylazo)-phenyl]-amino}-ethyl ester in N-methyl-2-pyrrolidone was uniformly mixed with 10.1 grams of the "3M PREMIUM BODY FILLER PART No. 50597" from 3M Company. The resulting body filler was pink. 0.21 grams of the "BENOX B-50" hardener was then uniformly mixed on a palette for 90 seconds at 21° C. with the pink body filler. The resulting pink material was spread out on the palette to an approximate thickness of ⅛-¼ inches (3.18-6.35 mm). After 9 minutes, a hardened white body filler was obtained with no residual pink color.

Composition Example 6

75 μL of a 5.0 mg/mL solution of allyl-carbamic acid 2-{(2-cyano-ethyl)-[4-(6-nitro-benzothiazol-2-ylazo)-phenyl]-amino}-ethyl ester in N-methyl-2-pyrrolidone was uniformly mixed with 10.1 grams of the "3M PREMIUM BODY FILLER PART No. 50597" from 3M Company. The resulting body filler was pink. 0.21 grams of the "BENOX B-50" hardener was then uniformly mixed on a palette for 90 seconds at 21° C. with the pink body filler. The resulting pink material was spread out on the palette to an approximate thickness of ⅛-¼ inches (3.18-6.35 mm). After 7 minutes, a hardened white body filler was obtained with no residual pink color.

Illustrative Example A

100 μL of a 6.5 mg/mL solution of acrylic acid 1-(4-phenylazo-phenylazo)-naphthalen-2-yl ester in tetrahydrofuran was uniformly mixed with 10.0 grams of the "3M PREMIUM BODY FILLER PART No. 50597" from 3M Company. The resulting body filler was beige. 0.20 grams of the "BENOX B-50" hardener was then uniformly mixed on a palette for 45 seconds at 21° C. with the beige body filler. The resulting beige material was spread out on the palette to an approximate thickness of ⅛-¼ inches (3.18-6.35 mm). After 6 minutes, a hardened beige body filler was obtained with no change in color. After 12 minutes, the fully cured body filler was still beige in color with no noticeable fade from the original beige color.

Illustrative Example B

200 μL of a 20.0 mg/mL solution of 4-(4-nitrophenylazo)-N-(2-cyanoethyl)-N-(acetoxyethyl)aniline in N-methyl-2-pyrrolidone was uniformly mixed with 9.99 grams of the "3M PREMIUM BODY FILLER PART No. 50597" from 3M Company. The resulting body filler was light orange. 0.20 grams of the "BENOX B-50" hardener was then uniformly mixed on a palette for 45 seconds at 21° C. with the light orange body filler. The resulting light orange material was spread out on the palette to an approximate thickness of ⅛-¼ inches (3.18-6.35 mm). After 6 minutes, a hardened light orange body filler was obtained with no change in color. After 12 minutes, the fully cured body filler was still light orange in color with no noticeable fade from the original light orange color.

4-(4-Nitrophenylazo)-N-(2-cyanoethyl)-N-(acetoxyethyl) aniline can be obtained from SinoChemexper Company of Sinochem Group, Beijing, China.

Various modifications and alterations of this disclosure may be made by those skilled the art without departing from the scope and spirit of the disclosure, and it should be understood that this invention is not to be unduly limited to the illustrative embodiments set forth herein.

What is claimed is:
1. A compound represented by formula:

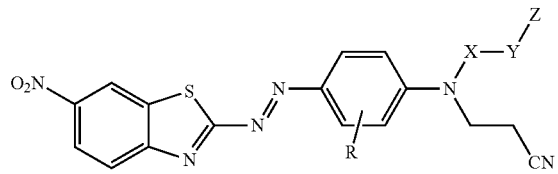

wherein
R is hydrogen or alkyl;
X is alkylene;
Y is a bond, ether, thioether, amine, amide, ester, thioester, carbonate, thiocarbonate, carbamate, thiocarbamate, urea, thiourea, alkylene, arylalkylene, alkylarylene, or arylene, wherein alkylene, arylalkylene, alkylarylene, and arylene are optionally at least one of interrupted or terminated by at least one of an ether, thioether, amine, amide, ester, thioester, carbonate, thiocarbonate, carbamate, thiocarbamate, urea, or thiourea; and
Z is an acrylate, a methacrylate, an acrylamide, a methacrylamide, a styrenyl, or a terminal alkenyl having at least three carbon atoms.

2. The compound of claim 1, wherein Z is acrylate, methacrylate, or styrenyl.

3. The compound of claim 2, wherein Y is a bond, —O—, —O—C(O)—, —O—C(O)—NR$^1$—, or alkylene optionally at least one of interrupted or terminated by at least one ether, ester, carbonate, or carbamate, and wherein R$^1$ is hydrogen, alkyl, aryl, arylalkylenyl, or alkylarylenyl.

4. The compound of claim 3, wherein —X—Y—Z is —CH$_2$CH$_2$—O—C(O)—CH=CH$_2$, —CH$_2$CH$_2$—O—C(O)—C(CH$_3$)=CH$_2$, or —CH$_2$CH$_2$—O—C(O)—C$_6$H$_4$—CH=CH$_2$.

5. A composition comprising the compound of claim 1, a free radical initiator, and a diluent.

6. The composition of claim 5, wherein the free-radical initiator is an organic peroxide.

7. The composition of claim 5, wherein the free-radical initiator is a photoinitiator.

8. A composition comprising the compound of claim 1 and a curable polymeric resin.

9. The composition of claim 8, wherein the curable polymeric resin is an unsaturated polyester resin.

10. The composition of claim 8, further comprising at least one of styrene monomer, a substituted styrene monomer, an acrylate monomer, a methacrylate monomer, an acrylamide monomer, or a methacrylamide monomer.

11. The composition of claim 8, further comprising at least one of ceramic beads, polymer beads, silica, hollow ceramic elements, hollow polymeric elements, alumina, zirconia, mica, dolomite, woolasonite, fibers, talc, calcium carbonate, sodium metaborate, or clay.

12. A method for indicating extent of cure of a curable polymeric resin, the method comprising:
providing a composition comprising a curable polymeric resin, a free-radical initiator, and a compound of claim 1 in an amount sufficient to provide the composition with a first absorbance at a wavelength in a range from 400 nanometers to 700 nanometers; and
allowing the composition to cure to provide a cured composition, wherein the cured composition has a second absorbance at the wavelength that is different from the first absorbance, and
determining a difference between the first absorbance and the second absorbance, wherein the difference between the first absorbance and the second absorbance indicates the extent of cure of the curable polymeric resin.

13. The method of claim 12, wherein the difference between the first absorbance and the second absorbance is visually determined.

14. The method of claim 12, wherein providing the composition comprises mixing the curable polymeric resin with a curative comprising the free-radical initiator and the compound or wherein providing the composition comprises mixing the curable polymeric resin and the compound and then combining the free-radical initiator with the curable polymeric resin and the compound, and wherein mixing is carried out until the composition is uniformly colored.

15. The method of claim 12, wherein the curable polymeric resin is an unsaturated polyester resin, and wherein the composition further comprises at least one of styrene monomer, a substituted styrene monomer, an acrylate monomer, a methacrylate monomer, an acrylamide monomer, or a methacrylamide monomer.

16. The method of claim 12, wherein the free-radical initiator is an organic peroxide.

17. The method of claim 12, wherein the free-radical initiator is a photoinitiator.

18. The method of claim 12, wherein Z in the compound represented by formula:

is acrylate, methacrylate, or styrenyl.

19. The method of claim 18, wherein Y in the compound represented by formula:

is a bond, —O—, —O—C(O)—, —O—C(O)—NR$^1$—, or alkylene optionally at least one of interrupted or terminated by at least one ether, ester, carbonate, or carbamate, and wherein R$^1$ is hydrogen, alkyl, aryl, arylalkylenyl, or alkylarylenyl.

20. The method of claim 19, wherein —X—Y—Z in the compound represented by formula:

is —CH$_2$CH$_2$—O—C(O)—CH=CH$_2$, —CH$_2$CH$_2$—O—C(O)—C(CH$_3$)=CH$_2$, or —CH$_2$CH$_2$—O—C(O)—C$_6$H$_4$—CH=CH$_2$.

* * * * *

UNITED STATES PATENT AND TRADEMARK OFFICE
CERTIFICATE OF CORRECTION

PATENT NO. : 9,772,321 B2
APPLICATION NO. : 14/777033
DATED : September 26, 2017
INVENTOR(S) : Michael Wendland It is certified that error appears in the above-identified patent and that said Letters Patent is hereby corrected as shown below:

In the Specification

Column 7
Line 39, delete "woolasonite," and insert -- wollastonite, --, therefor.

Column 8
Line 7 (approx.), delete "HOLLLOW" and insert -- HOLLOW --, therefor.

Column 11
Line 46, delete "woolasonite," and insert -- wollastonite, --, therefor.

Column 12
Line 55 (approx.), delete "woolasonite," and insert -- wollastonite, --, therefor.

In the Claims

Column 21
Line 29, in Claim 11, delete "woolasonite," and insert -- wollastonite, --, therefor.

Signed and Sealed this
Eighth Day of June, 2021

Drew Hirshfeld
*Performing the Functions and Duties of the*
*Under Secretary of Commerce for Intellectual Property and*
*Director of the United States Patent and Trademark Office*